US009958382B2

United States Patent
Denk et al.

(10) Patent No.: US 9,958,382 B2
(45) Date of Patent: May 1, 2018

(54) METHOD FOR DETERMINING THE ABRASION RESISTANCE OF AT LEAST ONE WEAR LAYER ARRANGED ON A CARRIER PLATE

(71) Applicant: Flooring Technologies Ltd., Kalkara (MT)

(72) Inventors: Andre Denk, Wittstock/Dosse (DE); Norbert Kalwa, Horn-Bad Meinberg (DE)

(73) Assignee: Flooring Technologies Ltd., Kalkara (MT)

( * ) Notice: Subject to any disclaimer, the term of this patent is extended or adjusted under 35 U.S.C. 154(b) by 0 days. days.

(21) Appl. No.: 15/564,594

(22) PCT Filed: Mar. 21, 2016

(86) PCT No.: PCT/EP2016/056125
§ 371 (c)(1),
(2) Date: Oct. 5, 2017

(87) PCT Pub. No.: WO2016/162196
PCT Pub. Date: Oct. 13, 2016

(65) Prior Publication Data
US 2018/0080867 A1    Mar. 22, 2018

(30) Foreign Application Priority Data

Apr. 9, 2015   (EP) ..................................... 15162969
Nov. 26, 2015  (WO) ................. PCT/EP2015/077775

(51) Int. Cl.
*G01N 21/35*     (2014.01)
*G01N 21/359*    (2014.01)
(Continued)

(52) U.S. Cl.
CPC ............. *G01N 21/359* (2013.01); *G01N 3/56* (2013.01); *G01N 2021/8427* (2013.01)

(58) Field of Classification Search
CPC ........................ G01N 21/3554; G01N 21/359
See application file for complete search history.

(56) References Cited

U.S. PATENT DOCUMENTS 5,965,888 A * 10/1999 Engstrom ............. B27N 1/029
                                              250/339.07
9,759,653 B2 *  9/2017 Kalwa ................ G01N 21/3554
(Continued)

FOREIGN PATENT DOCUMENTS

DE   102009037541 A1   2/2011
EP       2338693 A1    6/2011
(Continued)

OTHER PUBLICATIONS

English Translation of ISR for PCT/EP2016/056125, dated Dec. 26, 2017.*

*Primary Examiner* — Casey Bryant
(74) *Attorney, Agent, or Firm* — The Webb Law Firm

(57) ABSTRACT

A method for determining the abrasion resistance of at least one wear layer arranged on a carrier plate, including: capturing at least one NIR spectrum of the wear layer arranged on the at least one carrier plate using at least one NIR detector and determining the abrasion resistance of the at least one wear layer by comparing the NIR spectrum for the abrasion resistance that is to be determined with at least one NIR spectrum ascertained for at least one reference sample by multivariant data analysis (MDA).

20 Claims, 5 Drawing Sheets

(51) Int. Cl.
*G01N 3/56* (2006.01)
*G01N 21/84* (2006.01)

(56) References Cited

U.S. PATENT DOCUMENTS

| 2006/0091577 | A1* | 5/2006 | Shen | ........................ | B27N 1/00 |
|---|---|---|---|---|---|
| | | | | | 264/109 |
| 2011/0217463 | A1 | 9/2011 | Oldorft | | |
| 2016/0123871 | A1 | 5/2016 | Kalwa et al. | | |

FOREIGN PATENT DOCUMENTS

| EP | 2808636 | A1 | 3/2014 |
|---|---|---|---|
| EP | 2915658 | A1 | 9/2015 |

* cited by examiner

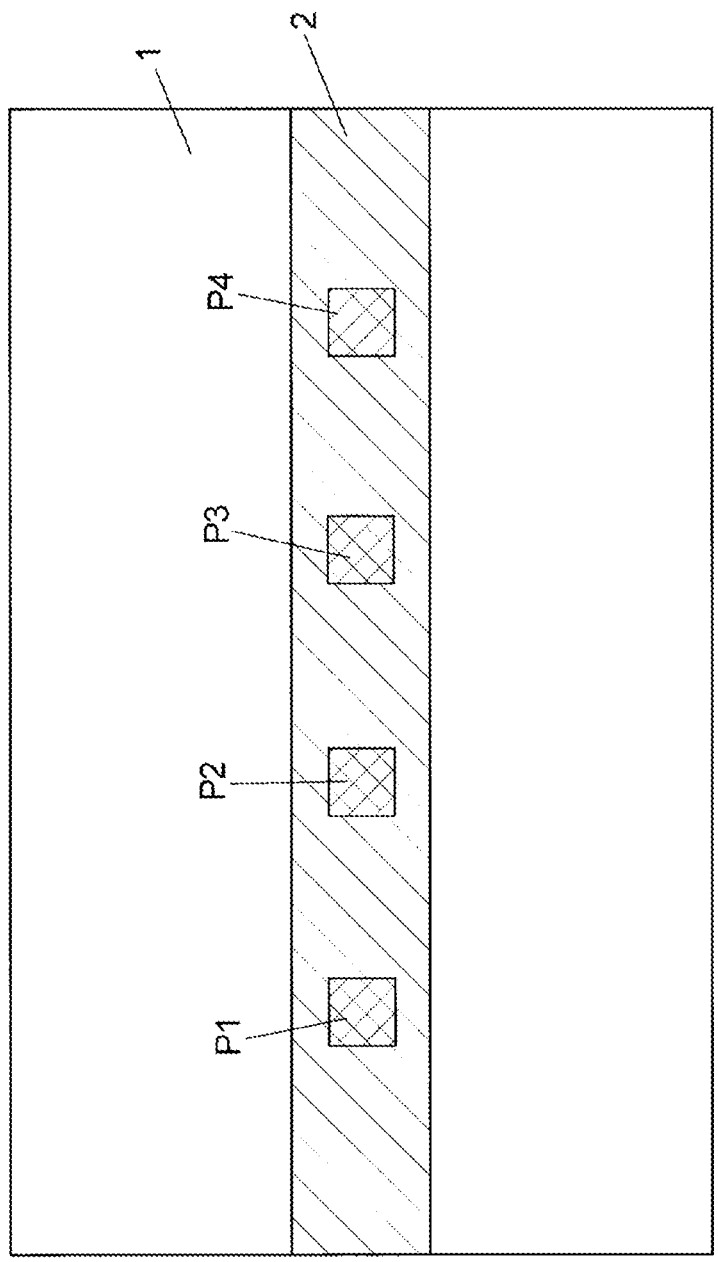

METHOD FOR DETERMINING THE ABRASION RESISTANCE OF AT LEAST ONE WEAR LAYER ARRANGED ON A CARRIER PLATE

CROSS-REFERENCE TO RELATED APPLICATIONS

This application is the United States national phase of International Application No. PCT/EP2016/056125 filed Mar. 21, 2016, and claims priority to European Patent Application No. 15162969.8 filed Apr. 9, 2015, and International Application No. PCT/EP2015/077775 filed Nov. 26, 2015, the disclosures of which are hereby incorporated in their entirety by reference.

BACKGROUND OF THE INVENTION

Field of the Invention

The present invention relates to a method for determining the abrasion resistance of at least one wear layer arranged on a core board, the use of an NIR detector for determining the abrasion resistance of the wear layer applied on a core board, and a device for implementing the method.

Description of Related Art

Wood-composite boards are used as supportive materials in a very wide variety of sectors: wood-composite boards are known inter alia from the use as floor panels, e.g. in the form of laminate floors. These boards are usually produced from wood fibers or wood particles, or from strands. Laminate floors by way of example use high-density fiberboard produced from wood fibers with a wide variety of decorative effects.

In particular when wood-composite boards are used as laminate floors, it is desirable and necessary to protect the decorative surfaces from abrasion and wear by applying suitable wear layers. Wear layers used are in particular hardenable lacquers based on acrylic resin, on epoxy resin or on melamine resins.

A known method of improving wear-resistance and scratch-resistance properties is embedment, into these resin layers, of suitable particles in the size range from 25 nm to 150 pm. The larger particles here serve to improve abrasion resistance, and the smaller particle serve to improve scratch resistance. Particles can by way of example be nanoparticles made of silicon carbide, silicon dioxide or α-aluminum oxide. Determination of the abrasion resistance of the hardened wear layer is therefore a decisive quality-assurance criterion for the production of laminate floors.

In essence there are two possible approaches for the production of a wear layer on a suitable core board: the wear layer can consist of a paper-based structure or of a liquid-based structure. In the case of a paper-based structure, the wear layer consists of a thin transparent paper impregnated with a thermoset resin, e.g. a melamine-formaldehyde resin, and with wear-inhibiting particles. In the case of a liquid-based structure, the wear layer comprises a resin layer which likewise can comprise wear-inhibiting particles, e.g. corundum particles, and also other auxiliaries, e.g. glass beads or cellulose. In the case of the paper-based structure, the wear layer is then placed, with a likewise impregnated decorative sheet, onto the upper side of a wood-composite board; in the case of the liquid-based structure, the resin layer comprising the wear-inhibiting particles is applied in liquid form to a board which has already been base-coated and printed, or else to a paper sublayer already arranged on the board, and is dried.

The abrasion resistance of these wear layers depends mainly on the quantity of the abrasion-resistant particles introduced into the wear layer. In the case of the paper-based structure, the wear-inhibiting particles are applied by scattering onto the paper during impregnation, or a corundum-containing resin slurry is applied by use of rollers or other methods. In this case, the quantity of abrasion-resistant particles applied can be determined by simple methods, e.g. asking of the overlay, and specifically before the overlay paper is applied to the core board.

However, this method cannot be used in the case of a wear layer with liquid-based structure, because the wear-inhibiting particles are applied together with the liquid resin to a board that has already been base-coated and printed, and are dried. Determination of the quantity of abrasion-resistant particles by asking of the coating is difficult because of the basecoat applied, which comprises inorganic pigments.

One possibility for determining the quantity of abrasion-resistant particles in a wear layer in the form of a liquid-based structure consists in calculating the quantity of solid particles in the weighed-out quantity of liquid resin applied, starting from the known quantity of solid particles (e.g. corundum particles) in a resin batch, but this does not necessarily correspond to the actual value of the quantity of solid particles in the coating.

Another possible approach to determination of the abrasion resistance of hardened protective layers on laminate floors is in accordance with DIN EN 13329:2009 (D). Here, the ability of the service layer or wear layer to resist removal by wear is tested. Samples (e.g. measuring 10 cm×10 cm) are cut out from the board to be tested or from the design to be tested. These samples are clamped into a test rig which comprises a weight (500 g) and two swivelable arms with movable abrasion rollers. Standardized abrasive paper has been adhesive-bonded to the abrasion rollers. The clamped samples rotate under the abrasion wheels. After every 200 rotations, the abrasive paper is changed and surface wear is checked. The test ends when the substrate (printing base paper, basecoat) has become visible over an extent of in each case 0.6 mm² in three quadrants of the test specimen. The number of rotations required to expose the decorative effect is stated as result. The following abrasion classes are distinguished in DIN EN 13329 and are defined by increasing performance level:

| | Abrasion class | | | | |
|---|---|---|---|---|---|
| | AC1 | AC2 | AC3 | AC4 | AC5 |
| Number of revolutions | ≥900 | ≥1500 | ≥2000 | ≥4000 | ≥6000 |

In accordance with this definition, only about 900 revolutions are required to expose the decorative effect in abrasion class AC1. A wear layer of abrasion class AC1 accordingly has the lowest abrasion resistance.

However, the standardized test method described is very time-consuming, and merely provides individual values which are not representative of the entire production width: the test specimens measure only 10 cm×10 cm, and are usually only taken from the board produced at a few locations. In order to draw a conclusion relating to the entirety of the board produced, it would be necessary to divide the board into a multiplicity of test specimens, and to test all of these.

However, the test is very costly because of the expensive abrasive paper used in the test, and moreover sometimes takes more than an hour for the higher abrasion classes. By way of example, testing of a sample in abrasion class AC4 takes at least 90 minutes and costs at least 20 euros (merely for abrasive paper strips used). Products are spot-tested for wear resistance at least three times a day on production lines for purposes of quality monitoring. Three samples are studied in each abrasion-resistant test (in accordance with DIN EN 13329).

The table below collates the minimal time required and expense for abrasion-resistance testing on one day on a production plant in accordance with DIN EN 13329 for a product in abrasion class AC4:

|  | Time required (hours) | Costs for materials (euros) |
| --- | --- | --- |
| One sample (AC4) | 1.5 | 20* |
| One test (three samples) | 3** | 60 |
| One day (three tests) | 7.5 | 180 |

*The price of an abrasive paper strip is 0.50 euro
**Two samples can be tested simultaneously Accordingly, routine wear-resistance monitoring on a production plant requires 7.5 hours per day, and the costs of materials amount to at least 180 euros.

In particular when a liquid-based structure is used for a wear layer (i.e. when resin and abrasion-resistant particles are applied in a liquid), production parameter changes can cause undesired variations in the application process and thus variations in wear resistance: by way of example, continuous take-off from, and addition of fresh material to, the application vessel can change the viscosity of the application medium. Temperature variations and applicator-roll wear can also adversely affect the application process. Variations in abrasion value can moreover arise through non-uniformity of quantity applied, and also through non-uniform distribution of the solids in the wear layer.

As already described above, because the supportive material in the present case is in particular a wood composite, in particular medium- or high-density fiberboard, it is not possible to use any of the methods that are used by way of example in paper impregnation: a factor militating against use of IR radiation is that the radiation cannot penetrate the supportive material. Other technologies such as X-ray fluorescence likewise have only limited usefulness because these demand increased safety standards in respect of protection from radiation.

The present invention is therefore based on the technical object of providing a simple but efficient method which can determine or predict, with sufficient precision, the abrasion resistance of a core board (in particular a wood-composite board) provided with a wear layer. Determination of abrasion resistance of the wear layer here is intended to be possible not only after pressing and hardening of wear layer and core board, on the basis of the hardened wear layer, but also before pressing and hardening of the wear layer. The method should moreover not require any increased safety standards in the engineering of the plant, and should minimize susceptibility to error.

SUMMARY OF THE INVENTION

Accordingly, a process is provided for determining the abrasion resistance of at least one wear layer arranged on a core board. The present process comprises the following steps:
 recording at least one NIR spectrum of the wear layer arranged on the at least one core board
  a) before hardening of the at least one wear-protection layer,
  b) after hardening of the at least one wear layer, or
  c) before and after hardening of the at least one wear layer with use of at least one NIR detector in the wavelength range from 500 nm to 2500 nm, preferably from 700 nm to 2000 nm, with particular preference from 900 nm to 1700 nm;
 by means of multivariate data analysis (MDA), determining the abrasion resistance of the at least one wear layer by comparing the NIR spectrum recorded for determining the abrasion resistance of the at least one wear layer with at least one NIR spectrum recorded for at least one reference sample of the at least one wear layer with known abrasion resistance,
 where the at least one NIR spectrum recorded for the at least one reference sample with known abrasion resistance of the at least one wear layer has been determined in advance a) after hardening or b) before and after hardening with use of the same NIR detector in the wavelength range from 500 nm to 2500 nm, preferably from 700 nm to 2000 nm, with particular preference from 900 nm to 1700 nm.

The present process accordingly permits determination of the abrasion resistance of a wear layer arranged on a core board, where the abrasion resistance in particular is a function of the quantity of abrasion-resistant particles present in the wear layer.

A significant aspect of the present method is that the abrasion resistance of the wear layer is determined not only before hardening of the wear-protection layer but also after hardening of the wear-protection layer, and also in combination (twice) before and after hardening of the layer. With use of the NIR detector and with the aid of NIR radiation, an NIR spectrum of the wear layer applied to the core board is generated, and thus an NIR spectrum with specific peaks (absorption bands) is generated for the applied layer, varying with concentration and quantity of same. The procedure here is that the NIR radiation passes through the sample and in turn is reflected at the core and detected at the measurement head. Several hundred NIR measurements are made in a few seconds (e.g. up to fifteen NIR measurements in one second), and statistical validity of the values is thus ensured. The present method for determining the abrasion resistance of a wear layer arranged on a core board with use of an NIR detector makes use of the fact that the NIR radiation does not pass through the entire core board, i.e. through wear layer and core board, but instead is reflected at the surface. In particular, the NIR measurement in the present case of a wear layer is made in diffuse reflection. In diffuse reflection most of the incident light is reflected in all possible directions at the sample surface. Some of the incident light passes through the sample layers close to the surface and is absorbed there, and the remainder undergoes diffuse scattering. The radiation reflected from the surface or from the region close to the surface is detected by the NIR detector and used for determining the abrasion resistance. The NIR spectrum recorded includes not only information on the chemical properties of the sample from absorption by chemical bonds, e.g. in the resin, but also information, derived from scattering, relating to the physical nature of the exterior surface layers of the support.

In a first embodiment of the present method, the abrasion resistance of the at least one wear layer is determined before hardening of the wear layer within the production line for the boards, i.e. on-line. Accordingly, in this on-line variant the abrasion resistance is determined while the production process is proceeding. This permits direct control and intervention in the production process.

In a second embodiment of the present method, the abrasion resistance of the at least one wear layer is determined after hardening of the wear layer outside of the production line for the board (i.e. off-line). Accordingly, in this variant a finished pressed and hardened board is taken, or diverted, from the production line and tested off-line, e.g. in a separate laboratory in the context of routine quality monitoring.

This variant for testing the wear layer of a hardened coating on a board, e.g. a high-density fiberboard, with the aid of NIR spectroscopy provides an alternative to the time-consuming and costly abrasion-resistance testing described above in accordance with DIN EN 13329: wear resistance is tested with the aid of laboratory NIR test equipment in less than one minute, and this permits high sample throughput. The test is moreover non-destructive. The test results are stored automatically in electronic form, and are available for possible further use. Samples from a number of plants can moreover quickly be tested for wear resistance. Replacement of the wear-resistance test in accordance with DIN EN 13329 in the context of routine quality assurance by NIR measurement also reduces costs of materials and the time required to carry out the test, and significantly increases the scope of spot-testing. The time-consuming and costly abrasion-resistance test in accordance with DIN EN 13329 is used only for calibration and validation of the NIR measurement method.

Another significant aspect of this test is significantly fewer errors and variations in test results due to subjective assessment by the tester. These variations can easily be +/20%. These are caused firstly by difficulty in assessing extent of damage to the IP (initial point=first visible damage to the decorative effect of extent 0.6 mm$^2$) and secondly by incorrect assessment of the size of the abraded area. Indeed, very large (up to 30%) variations can occur during abrasion-resistance testing by means of a Taber Abraser (DIN EN 13329) when a number of test specimens are taken from a sample. The novel method moreover eliminates all variations in the abrasion strips used in the test and in the Taber Abraser (Shore hardness of rubber rollers, incorrect positioning of suction dust-removal system, etc.). The (24 h) conditioning specified for the test according to the standard is also no longer necessary. It is known that this has a considerable effect on the test result. The error/variation of the values measured by the NIR test equipment after calibration is significantly smaller: <10%.

In a third variant of the present method, the abrasion resistance of the at least one wear layer is determined before hardening of the wear layer within the production line and after hardening of the wear layer outside of the production line. This method variant therefore combines on-line (before hardening) with off-line (after hardening, e.g. laboratory measurement). It is advantageous here that the control interventions that are continuously possible within the production process as it proceeds are subjected to a degree of crosschecking/verification by the subsequent measurement in the laboratory. This is extremely important in particular in complex processes.

In a preferred embodiment of the present process, the reference sample with known abrasion resistance of the wear layer comprises a wear layer applied on a core board where core board and wear layer of the reference sample are of the same type as the test sample made of core board and wear layer; i.e. the test sample has the same type of composition as the reference sample.

In another embodiment of the present method, the abrasion resistance of the wear layer of the reference sample is determined before or after hardening of same on the basis of at least a single sample taken from the reference sample. The abrasion resistance of the wear layer of the reference sample here is preferably determined on the basis of at least one, preferably at least four or more, individual samples taken from the reference sample. The abrasion resistance of the individual samples of the reference sample here is in particular determined in accordance with DIN EN 13329:2009 (D).

Calibration is achieved in the present method by recording two NIR spectra of a core board coated with a wear layer.

In a first variant, calibration uses a core board which has been provided with the wear layer and has already been pressed and hardened. The NIR equipment used for calibration records NIR spectra of samples with various decorative effects and board thicknesses. Once the NIR spectra have been recorded, the abrasion resistance of the samples is tested (in accordance with the standard method of DIN EN 13329 (e.g. DIN EN 13329:2009, D)).

In a second variant, calibration takes place before hardening and pressing, i.e. on the basis of a coated core board that has not yet been hardened and pressed and that is tested for abrasion resistance after the procedure of pressing and curing, the method here being as follows: a core board that has been previously base-coated and printed (e.g. a wood-composite core board) is coated with a wear layer comprising abrasion-resistant particles. An NIR spectrum of the board provided with the wear layer is recorded before the procedure of pressing and hardening. The board is then pressed, for example in a short-cycle press, with resultant full hardening of the wear-protection layer. After cooling of the board provided with the wear layer, a number of individual samples are taken for abrasion-resistance testing; it is preferable here that the individual samples for abrasion-resistance testing are taken at those locations of the coated wood-composite board where the NIR spectrum was previously recorded. The abrasion resistance of the individual samples is determined in accordance with the standard method of DIN EN 13329:2009 (D) described above for laminate floors.

The abrasion values respectively determined are used to calculate an average value, which is attributed to the respective NIR spectrum. This method is used to record a number of reference spectra of coated boards with differently colored decorative effects. The reference spectra are used to establish a calibration model which can be used to determine the abrasion resistance of an unknown sample. In the case of decorative effects of very different colors, it is also conceivable to form respective clusters of decorative effects having similar coloring. The calibration model is established by means of multivariate data analysis (MDA), and it is useful here to undertake comparison and interpretation of the NIR spectra over the entire recorded spectral region. Multivariate analysis methods typically involve simultaneous study of a plurality of statistical variables. To this end, the number of variables in a data set is reduced while at the same time the information present therein is retained.

The multivariate data analysis in the present case is achieved by way of the partial least squares method (PLS regression), which is capable of establishing a suitable calibration model. Evaluation of the data obtained is preferably undertaken by using suitable analysis software, e.g. SIMCA-P analysis software from Umetrix AB or The Unscrambler from CAMO.

An advantage of recording an NIR spectrum in order to determine the abrasion resistance of wear layers is that the NIR detector can traverse the entire width of the board and can analyze particular problem regions. The measured values are moreover immediately available, and permit immediate intervention in the production process; in other methods this is not readily possible. The present method permits use of an automatically regulated system with alarm signaling and with automatic appropriate adjustment of abrasion resistance of the product via automatic appropriate adjustment of the quantity of abrasion-resistant particles applied, starting from an NIR measurement.

The present method therefore has a number of advantages: non-destructive continuous determination of the abrasion resistance of the wear-protection layer, and an automatically regulated system with alarm signalling, and measurement across the entire production width.

In an embodiment of the present method, the at least one wear layer is selected from the group comprising
a) at least one heat-curable protective layer, and/or
b) at least one UV-curable and/or electron-beam-curable (EBC) protective layer.

In a particularly preferred embodiment of the present method, a heat-curable resin layer a) is used as wear layer. The heat-curable resin layer here can comprise not only the abrasion-resistant particles but also natural and/or synthetic fibers, and also other additives. This heat-curable resin layer is also termed liquid overlay. The heat-curable resin is preferably a formaldehyde-containing resin, in particular a melamine-formaldehyde resin, a melamine-urea-formaldehyde resin or a urea-formaldehyde resin.

The abrasion-resistant particles present in the at least one wear layer, for example in the heat-curable resin layer, are in particular selected from the group comprising aluminum oxides (e.g. corundum), boron carbides, silicon dioxides (e.g. glass beads), silicon carbides.

As mentioned, the wear layer, e.g. in the form of a heat-curable resin layer, can also comprise natural or synthetic fibers selected from the group comprising wood fibers, cellulose fibers, partially bleached cellulose fibers, wool fibers, hemp fibers and organic or inorganic polymer fibers. Other additives that can be added are flame retardants and/or luminescent substances. Suitable flame retardants can be selected from the group comprising phosphates, borates, in particular ammonium polyphosphate, tris(tribomoneopentyl) phosphate, zinc borate and boric acid complexes of polyhydric alcohols. Luminescent substances used can be fluorescent or phosphorescent substances, in particular zinc sulfite and alkali metal aluminates.

A process for producing a wear layer in the form of a heat-curable resin layer (liquid overlay) is described inter alia in EP 233 86 93 A1. In the example described therein, after cleaning of the surface of a wood-composite board, a first upper resin layer comprising abrasion-resistant particles (e.g. corundum particles) is applied to a wood-composite board as core board, this first resin layer is dried, e.g. to a residual moisture level of from 3-6% by weight, a second resin layer comprising cellulose fibers is then applied to the wood-composite board, the second resin layer is dried, or dried to some extent, e.g. to a residual moisture level of from 3 to 6% by weight, an at least third resin layer comprising glass particles is applied to the wood-composite board and then the third resin layer is dried to some extent, e.g. likewise to a residual moisture level of from 3 to 6% by weight, and finally the layer structure is pressed with exposure to heat.

The at least one wear layer, e.g. in the form of the heat-curable resin layer described here, can accordingly comprise at least two sublayers, preferably at least three sublayers applied in succession. The quantity applied of the sublayers here is identical or different, and can be respectively from 1 to 50 $g/m^2$, preferably from 2 to 30 $g/m^2$, in particular from 5 to 15 $g/m^2$.

The liquid overlay is preferably applied to the upper side of the wood-composite board; it is preferable to apply a liquid counterbalancing layer to the reverse side of the wood-composite board.

Variant b) of the present wear-protection layer provides that this takes the form of a UV-curable and/or electron-beam-curable (EBC) protective layer. Radiation-curable, acrylate-containing lacquers can in particular be used for this purpose. The radiation-curable lacquers used as wear layer typically comprise methacrylates, e.g. polyester (meth)acrylates, polyether (meth)acrylates, epoxy (meth)acrylates or urethane (meth)acrylates. It is also conceivable that the acrylate used or the acrylate-containing lacquer comprises substituted or unsubstituted monomers, oligomers and/or polymers, in particular in the form of acrylic acid, of acrylic ether and/or of acrylate monomers, acrylate oligomers or acrylate polymers.

One embodiment preferably provides more than one radiation-curable protective layer, preferably two or three protective layers or wear layers, which are respectively arranged on one another or applied on one another. In such cases, the quantity applied for each individual protective layer or each individual sublayer of a protective layer can vary from 10 $g/m^2$ to 50 $g/m^2$, preferably from 20 $g/m^2$ to 30 $g/m^2$ or can be identical. The total quantity applied of the wear layer can vary with the number of sublayers from 30 $g/m^2$ to 150 $g/m^2$, preferably from 50 $g/m^2$ to 120 $g/m^2$.

The at least one wear-protection layer can also comprise chemical crosslinking agents, e.g. based on isocyanates; adhesion between the individual mutually superposed wear-protection layers is thus increased.

As already described for the heat-curable resin layer, the radiation-curable protective layer can also comprise not only the abrasion-resistant particles but also natural and/or synthetic fibers and other additives. The acrylate compound used in the radiation-curable wear-protection layer is capable, because of its reactivity, of binding to, or coating of, the fibers, abrasion-resistant particles or additives present in the protective layer. During the pressing of the wood-composite boards at elevated temperature, the effect of heat causes chemical crosslinking of the reactive double bond of the acrylate compounds and thus formation of an antibleaching polymer layer on the fibers, particles, color pigments or additives.

In an embodiment of the present method, the at least one wear layer comprises a quantity of from 5 to 100 $g/m^2$ of abrasion-resistant particles, preferably from 10 to 70 $g/m^2$, with particular preference from 20 to 50 $g/m^2$. As the quantity of abrasion-resistant particles in the wear layer increases, the abrasion resistance thereof also increases, and therefore determination of the abrasion resistance with use of the present method also indirectly permits determination of the quantity of abrasion-resistant particles.

The thickness of the wear layer to be tested by means of the present method can be from 10 to 150 μm, preferably from 20 to 100 μm, with particular preference from 30 to 80 μm.

In a variant of the present method, the core board used is a wood-composite board, in particular a medium-density fiberboard (MDF), high-density fiberboard (HDF) or coarse particleboard (CPB) or plywood board, a cement fiberboard and/or gypsum fiberboard, a magnesium oxide board, a wood-plastic board, in particular a wood-plastic-composite (WPC) board and/or a plastics board.

One variant provides, arranged between the core board and the at least one wear layer, at least one basecoat layer and at least one decorative layer.

The basecoat layer preferably used here comprises a composition made of casein as binder, and comprises inorganic pigments, in particular inorganic color pigments. Color pigments that can be used in the basecoat layer are white pigments such as titanium dioxide, or else other color pigments, for example calcium carbonate, barium sulfate or barium carbonate. The basecoat can also comprise water as solvent alongside the color pigments and the casein. It is likewise preferable that the pigmented base layer applied consists of at least one, preferably of at least two, with particular preference of at least four, sublayers or applications applied in succession, where the quantity applied in the sublayers or applications can be identical or different.

After application of the basecoat layer, this is dried in at least one convection dryer. If a plurality of basecoat layers or basecoat sublayers are applied, in each case a drying step takes place correspondingly after application of the respective basecoat layer or basecoat sublayer. It is likewise conceivable that after each drying step for a basecoat layer there is/are one or more grinding assemblies provided for grinding the basecoat layers.

In another embodiment of the method here for the case of application of at least one basecoat layer to the core board, it is possible to apply at least one primer layer to same, e.g. in the form of a UV flatcoat or EBC flatcoat.

The decorative layer already mentioned above can be applied by means of direct printing. In the case of direct printing, a water-based pigmented printing ink is applied in the intaglio process or in the digital printing process; the water-based pigmented printing ink can be applied in more than one layer, e.g. in the form of from two to ten layers, preferably from three to eight layers.

In the case of direct printing, the at least one decorative layer is, as mentioned, applied by means of an analogous intaglio process and/or of a digital printing process. The intaglio process is a printing technique in which the elements to be replicated take the form of depressions in a printing template which is inked before printing. The printing ink is mainly located in the depressions and is transferred to the article to be printed, e.g. a wood-fiber core board, by virtue of pressure applied to the printing template and of adhesion forces. In the case of digital printing, in contrast, the printed image is transferred directly from a computer to a printing machine, e.g. a laser printer or inkjet printer. No static printing template is used here. In both processes it is possible to use aqueous inks or UV-based colorants. It is likewise conceivable to combine the intaglio and digital printing techniques mentioned. A suitable combination of the printing techniques can be achieved directly on the core board or on the layer to be printed, or else can be achieved before printing via appropriate modification of the electronic data sets used.

The core board provided with a wear layer in the form of a liquid overlay layer (variant a) or with a radiation-curable protective layer (variant b) can likewise be provided with a 3D embossment structure, where the surface structure is preferably applied by embossing in a short-cycle press, optionally synchronously with the decorative effect. The 3D structure is preferably embossed or impressed by means of suitable embossment structures. The structured effects can be achieved with use of structured lacquer rolls, structured calenders, or structured press plates.

The present method therefore permits determination of the abrasion resistance of a wood-composite board with the following layer structure: wood-fiber core board/basecoat layer/primer layer/decorative layer/wear layer. Each of these layers can consist of one or more sublayers. On the reverse side of the wood-fiber core board it is possible to apply a counterbalancing paper or a liquid counterbalancing layer and other sound-deadening layers. Sound-deadening layers that can be used are in particular crosslinked PE mats with thicknesses of 1.0 mm or filled heavy-gauge films of thickness from 0.3 to 3 mm, or else foamed PE films or foamed PU films.

In a particularly preferred embodiment of the present method, at least one heat-curable resin layer, which however comprises no abrasion-resistant particles, is applied to the underside of the wooden core board.

The present method for determining the abrasion resistance of a wear layer arranged on a core board is implemented in a device or production line or manufacturing line for producing boards which comprises at least device for applying at least one wear layer to a core board, e.g. a liquid overlay, at least one device for drying the wear layer and at least one NIR detector for implementing the method of the invention, where the arrangement of the at least one NIR detector a) is within, or as part of, the production line, in particular downstream of the applicator device and of the drying device in the direction of processing;
b) is outside of, or separate from, the production line, e.g. in a suitable test laboratory, or
c) is outside of and additionally within, or as part of, the production line, and in particular here downstream of the applicator device and of the drying device in the direction of processing.

In the latter case, accordingly, the arrangement has the at least one NIR detector in a production line or manufacturing line for the at least one board, comprising at least one applicator device for the wear layer to be applied, for example a roll, spray device or casting device, and at least one drying device, e.g. in the form of a convection dryer, IR dryer and/or NIR dryer.

In one variant, the present device or manufacturing line comprises a device for applying at least one resin layer to that side of the core board that is opposite to the wear layer, and a device for drying this at least one resin layer, where the arrangement has both devices upstream of the at least one NIR detector in the direction of processing.

With particular preference, the arrangement has the device for applying the at least one wear layer to the upper side of the core board and the device for applying the at least one resin layer to the underside of the core board parallel to one another, thus permitting simultaneous application of wear layer to the upper side and resin layer to the underside of the core board. By analogy with this, the arrangement of the respective drying devices for wear layer on the upper side and resin layer on the underside of the core board with respect to one another is likewise preferably such that the drying procedure takes place at the same juncture.

It is also conceivable that the device or manufacturing line for producing the boards comprises more than one applicator device for the wear layer and resin layer and more than one drying device for wear layer/resin layer, where the arrangement has the at least one NIR detector downstream of the final drying device in the direction of processing. In this type of case, the quantity applied per wear layer and per applicator device can be identical or can vary. If the wear layer has three sublayers by way of example the total quantity of wear layer can vary from 50 $g/m^2$ to 120 $g/m^2$, and can be from 25% by weight to 50% by weight per applicator device.

It is also conceivable that the present manufacturing line comprises applicator devices and drying devices for at least one basecoat layer and/or primer layer and also an applicator device for applying at least one decorative layer. In this case, the applicator device for a decorative layer can comprise a plurality of intaglio printing rollers (e.g. three or four printing rollers).

However, it is also conceivable that the manufacturing line uses no applicator devices and/or drying devices for basecoat layer, primer layer and/or decorative layer, and uses wood-composite boards that have already been pre-printed and placed into intermediate storage.

In one embodiment in which the NIR measurement takes place not only on-line but also off-line, or else only off-line, the structure of a manufacturing line is as follows:

a) a first applicator device for applying at least one first sublayer of a wear layer to the upper side of a core board, in particular of a printed core board, and at least one first sublayer of a resin layer (without abrasion-resistant particles) to the underside of the core board;
b) an IR assembly arranged downstream of the first applicator device in a direction of processing (where the IR assembly in particular serves to generate a predetermined minimal surface temperature and to provide a uniform surface temperature), and at least one first drying device (e.g. convection dryer) arranged downstream of the IR assembly in the direction of processing for drying the at least one first sublayer of the wear-protection layer and/or resin layer;
c) a second applicator device arranged downstream of the first drying device in the direction of processing, for applying at least one second sublayer of a wear layer to the upper side of the core board and at least one second sublayer of a resin layer to the underside of the core board;
d) a second drying device (e.g. convection dryer) arranged downstream of the second applicator device in a direction of processing, for drying the at least one second sublayer of the wear-protection layer and/or resin layer;
e) a third applicator device arranged downstream of the second drying device in the direction of processing, for applying at least one third sublayer of a wear-protection layer to the upper side of the core board and at least one third sublayer of a resin layer to the underside of the core board;
f) a third drying device (e.g. convection dryer) arranged downstream of the third applicator device in a direction of processing, for drying the at least one third sublayer of the wear-protection layer/resin layer;
g) optionally an NIR detector arranged downstream of the third drying device in the direction of processing, for on-line determination of the abrasion resistance of the wear layer arranged on the upper side of the core board;
h) a short-cycle press (SC press) arranged downstream of the NIR detector in the direction of processing, for pressing and hardening the wear layer arranged on the upper side of the core board and of the resin layer arranged on the underside of the core board, and
i) an NIR detector arranged separately from the production line, for off-line determination of the abrasion resistance of the wear layer arranged on the upper side of the core board.

The applicator devices used are preferably applicator rolls which permit application of the layers to the upper side or the underside of the core board. Preference is given to parallel application of wear layer to the upper side and resin layer to the underside of the wood-composite core board.

It is possible, of course, to vary the number of the applicator devices and drying devices as required by the manufacturing line: the SC press can by way of example be followed by a rotating cooler to cool the hardened wood-composite boards.

As can be discerned from what has been said above, the NIR measurement can take place on-line after the final resin application downstream of the corresponding convection dryer upstream of the SC press. Each individual board is measured on-line here by the NIR detector. Movement of the NIR detector perpendicularly to the direction of production permits measurement of the abrasion resistance across the entire production width. However, the NIR measurement can also take place exclusively or additionally off-line. NIR measurement therefore provides a continuous non-destructive test method for determining abrasion resistance, and permits immediate intervention in the process.

BRIEF DESCRIPTION OF THE DRAWINGS

The invention is explained in more detail by taking an inventive example with reference to the figures of the drawings.

FIG. 1 is a diagram of the individual samples taken as reference sample for calibrating a core board provided with a wear layer for the abrasion-resistance test;

DETAILED DESCRIPTION OF THE INVENTION

Figure 2A:
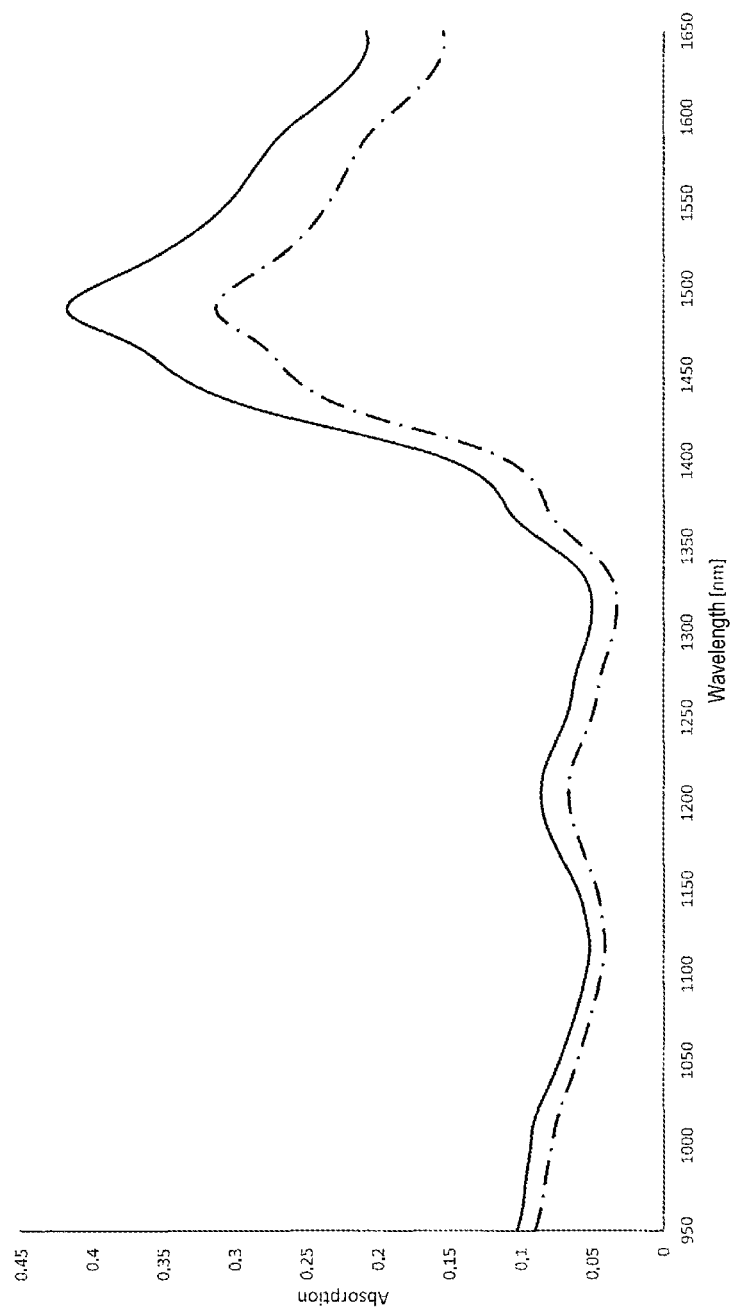
FIG. 2A shows NIR spectra measured for resin layers without wear-inhibiting particles applied on boards for furniture applications.

Inventive Example 1: Production of a Reference Sample and Calibration a) Calibration for an already hardened wear layer is achieved by recording an NIR spectrum of a core board as reference sample by analogy with the procedure described in b), where said board has been provided with an already hardened wear layer.
b) Calibration for an unhardened wear layer is achieved by recording an NIR spectrum of a core board as reference sample which is tested for abrasion resistance after the press procedure, where said board has been provided with a wear layer but has not yet been pressed.

To this end, a printed high-density fiberboard 1 is uniformly applicator-roll-coated from above in a coating plant with liquid melamine-formaldehyde resin comprising glass particles and corundum particles by way of a plurality of roll-applicator machines with intermediate drying. The quantity of the solid particles in the entire coating varies with abrasion class produced and is from 10 to 50 g/m². The diameter of the solid particles used is from 10 to 100 µm.

An NIR spectrum is recorded from the coated core board in a predetermined section 2 of the core board before the press procedure in the SC press.

The board is then pressed for 8 seconds at 200° C. and 40 bar in a short-cycle press. The protective layer is fully hardened here. After cooling of the board, a number (in particular four) of 10 cm×10 cm samples (P1-P4) are taken for abrasion-resistance testing. The samples for abrasion-resistance testing are taken in the board region 2, where the NIR spectrum was recorded (see FIG. 1).

The abrasion values are determined in accordance with the method of DIN EN 15468:2006 (directly coated laminate floors without overlay) with reference to DIN EN 13329, and an average value is calculated from the abrasion values and attributed to the NIR spectrum measured. This method is used to record a plurality of reference spectra of coated boards with various colored decorative effects. The reference spectra are used to establish a calibration model which can be used to determine or predict the abrasion resistance of an unknown sample. The calibration model is established by means of multivariate data analysis. This is achieved by using suitable analysis software, e.g. The Unscrambler analysis software from CAMO.

The NIR spectrum was recorded here in the wavelength range from 900 to 1700 nm. NIR measurement equipment from Perten was used to record the NIR spectra. The measurement head is a DA7400.

Inventive Example 2: On-Line Measurement of a Resin Coating with and without Wear Particles The measurement is achieved by recording NIR spectra of a predried synthetic resin layer (melamine resin) which has not yet been post-crosslinked in a short-cycle press, and which is present on a core board (e.g. HDF) that is tested for abrasion performance after the press procedure. A correlation was determined in advance by way of a calibration model via measurement of a large number of samples both spectroscopically and in accordance with the standard for determining abrasion resistance.

FIG. 2A shows two NIR spectra of two samples with different quantities of resin applied, which lead to different values during testing for abrasion performance. As can also be observed by using other spectroscopic methods, the samples, which differ in the quantity of the resin applied, exhibit a correlation between quantity and absorption. FIG. 2A shows measurements made with the aid of NIR spectroscopy on two boards for furniture applications; these boards were tested in accordance with DIN EN 14322: 2004—Wood-based panels—melamine faced boards for interior uses—6. Abrasion-resistance classification (upper, continuous curve) class 2 (IP>50 revolutions), (lower, dot-dash curve) class 1 (IP<50 revolutions). The spectra show the difference in abrasion performance, the fundamental reason for this difference being the different layer thickness of the melamine resin on the surface.

In the case of different quantities of resin applied, the NIR spectra differ mainly in the height of the baseline, but also in the absorption of the absorption band at about 1590 nm that is characteristic of the resin. As the result of abrasion performance testing improves (i.e. as the quantity of resin applied increases), the baseline and the N—H band become higher. The baseline of a spectrum here is the region without "meaningful peaks", which in the present case typically is in the region of the spectrum from 950 to 1350 nm. The basis of the NIR-spectroscopic method used here is as follows: the many reference spectra are used to establish a regression model by means of multivariate data analysis, and this model can be used to determine (predict) the abrasion resistance of an unknown sample. Establishment of a regression model achieves correlation between the spectral data and abrasion performance involving a small number of principal factors. The different quantity of synthetic resin is the main variance in the spectra here.

Figure 2B:
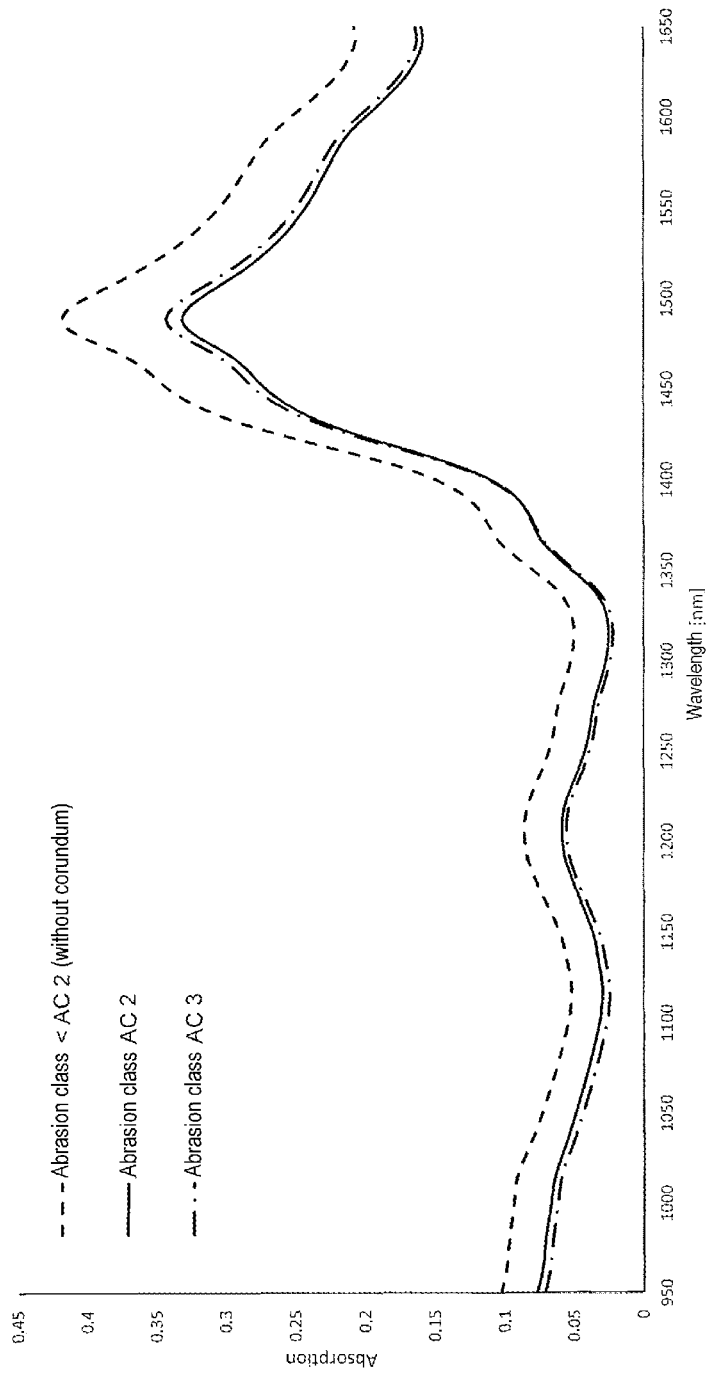
FIG. 2B shows NIR spectra measured for resin layers with and without wear-inhibiting particles applied on laminate floors.

FIG. 2B shows NIR spectra of three samples with identical quantity of resin applied, without corundum as wear particle or with different quantities of corundum.

FIG. 2B shows three NIR spectra of melamine-resin-coated samples which exhibit different results in abrasion performance testing. The samples were tested in accordance with DIN 15468 and DIN EN 13329: 2013—Laminate floor coverings—Elements with a surface layer based on aminoplastic thermosetting resins, Annex E. The wear class determined here in the abrasion performance test was as follows: for sample 1 (120 µm resin layer without corundum, upper, broken-line curve) below AC2, for sample 2 (120 µm resin layer with 20 g of corundum/m², lower, continuous curve) AC2, and for sample 3 (120 µm resin layer with 40 g of corundum/m², middle dot-dash curve) AC3. Samples 2 and 3 here therefore differ in the quantity of the wear-inhibiting particles.

In the NIR spectra presented, the scattering of the NIR light that occurs at the solid particles is superposed on the chemical information related to absorption. Alongside the small change in position of the baseline there is a slight discernible change of shape of the spectra, attributable to scattering at the solid particles. At increased solids content there is an increase in scattering particular at shorter wavelengths.

It is apparent by way of example that, despite greater quantities of resin at the surface, the baselines of the second set of spectra of FIG. 2B are lower than the baselines of the first set of spectra of FIG. 2A. This is attributable to the scattering at the corundum particles. The same considerations also apply to the distinct peak on the right-hand side of the spectrum.

Establishment of a regression model also takes into account the scattering of the NIR radiation at the solid particles, in addition to chemical information related to absorption, for determining abrasion performance. Accordingly, when the regression model is established, the spectroscopic data are considered in relation to the values obtained during testing of abrasion performance.

Because scattering of the NIR light at the solid particles plays a substantial part in the determination of abrasion performance, the primary factors considered are not only those that explain the chemical differences between the samples but also other primary factors which inter alia describe the morphology of the coating. The primary factors here are the peaks in the spectrum, scattering and change in position of the baseline.

Inventive Example 3: On-Line Measurement of a Lacquer Coating without Wear-Inhibiting Particles Two samples of wood-composites boards with different quantities of acrylate coating (13 g of lacquer/m$^2$ and 31 g/m$^2$) were provided for determining abrasion resistance of lacquer layers by means of NIR spectroscopy. Wear is determined in accordance with DIN EN 14978 by the "falling sand" test method.

Figure 3:
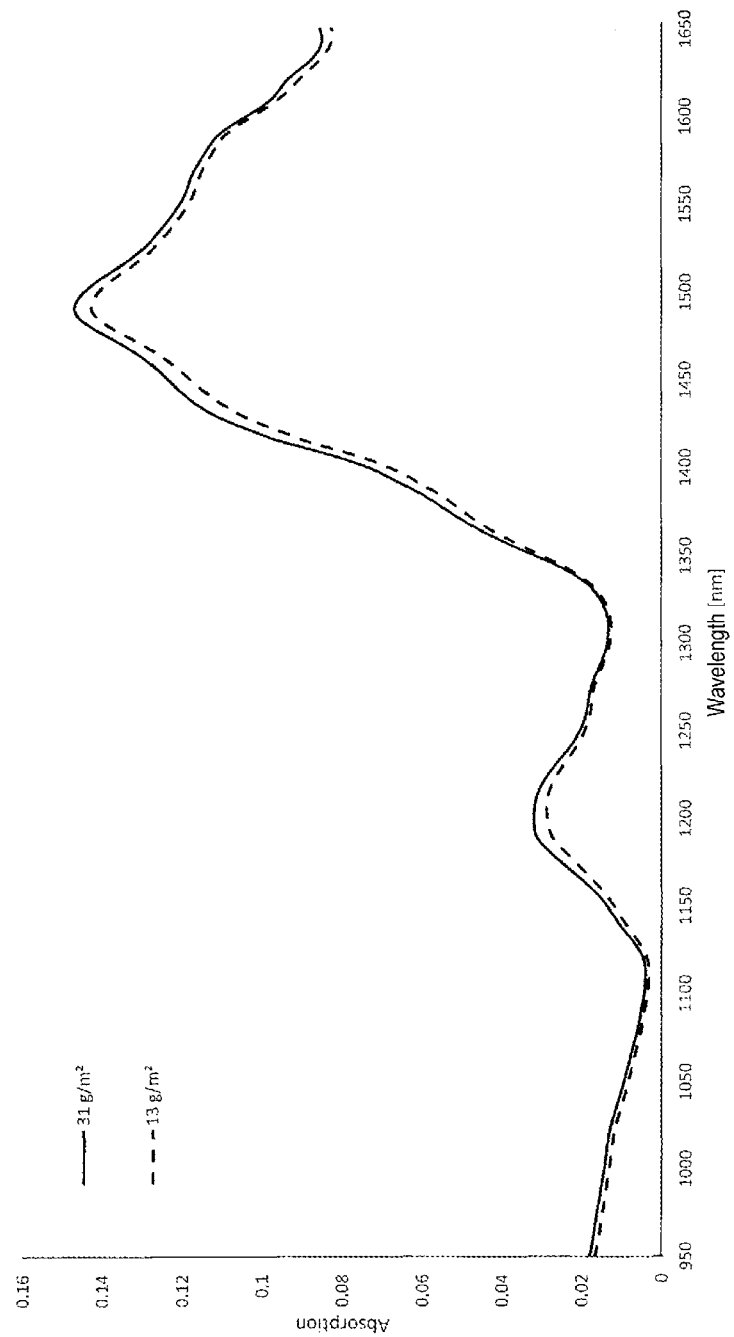
FIG. 3 shows NIR spectra measured for lacquer layers without wear-inhibiting particles.

FIG. 3 shows the NIR spectra for the two test samples: the upper, continuous curve corresponds to a quantity of 31 g/m$^2$ of lacquer, and the lower, broken-line curve corresponds to a quantity of 13 g/m$^2$ of lacquer. The NIR spectra differ mainly in the intensity of the absorption bands characteristic of an acrylate lacquer at about 1200 nm (2$^{nd}$ overtone of the C—H, C—H$_2$ and C—H$_3$ bonds) and at about 1590 nm (1st overtone of the amino groups). Here again, a relationship between quantity of lacquer and absorption is apparent. The larger quantity of lacquer exhibits slightly higher absorption than the smaller quantity of lacquer.

Inventive Example 4: Combination of On-Line and Off-Line Measurement

Figure 4:
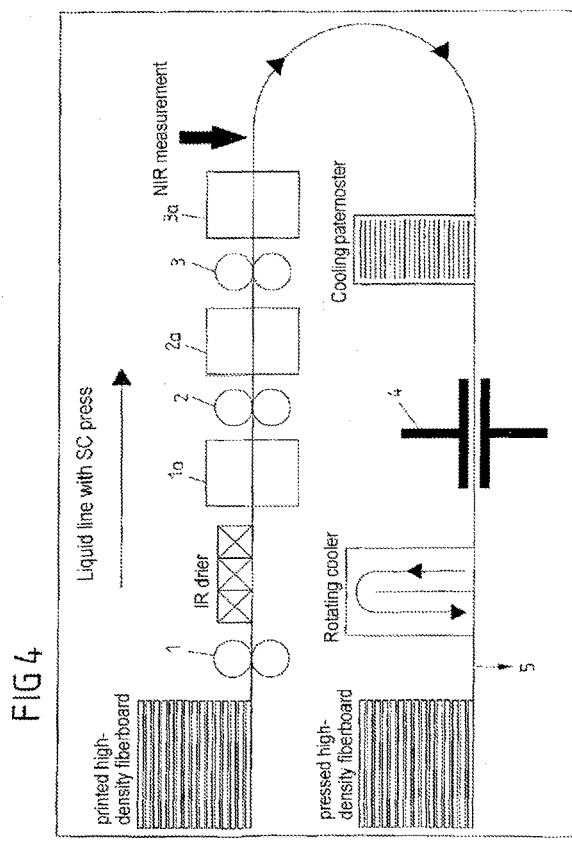
FIG. 4 is a diagram of a manufacturing line for a board with use of the method of the invention.

The measurement method is explained for the example of determination of abrasion resistance of a protective layer on a liquid line with SC press, depicted in the diagram in FIG. 4.

The liquid line processes high-density fiberboard with thickness 8 mm, width 2.07 m and length 2.80 m at 30 m/min. To this end, the boards are coated on the upper side in three applicator units (1 to 3) with a liquid melamine-formaldehyde resin comprising solid particles, and are coated from below with a liquid melamine-formaldehyde resin. The coating resin used is an aqueous melamine-formaldehyde resin with 60% by weight solids content.

After each application, the boards are dried at 200° C. in a hot-air dryer (1*a*-3*a*). The total quantity of the liquid overlay applied in the present inventive example after three applications varies with requirements from 50 g/m$^2$ to 120 g/m$^2$, and is divided as follows between the individual applicator units: AW1—50% by weight/AW2—25% by weight/AW3—25% by weight.

The NIR measurement follows the third convection dryer 3*a*. Each individual board here is measured on-line by the NIR detector, the motion of the NIR detector being perpendicular to the direction of production, thus permitting determination of abrasion resistance across the entire production width of the wood-composite board.

The coated wood-composite boards are then pressed in a short-cycle press 4 at 200° C. for 8 seconds. The specific pressure applied by the KT press is 40 kg/cm$^2$ (40 bar). The press and curing procedure is followed by cooling of the boards in a rotating cooler, and then the boards are stored or immediately passed to further use.

10×10 cm samples of the finished boards are used for routine determination of product quality of the pressed and hardened boards, and are crosschecked off-line by a laboratory measurement by laboratory NIR equipment 5. The laboratory measurement permits documentation of product quality.

NIR measurement therefore provides a non-destructive continuous measurement method for determining the abrasion resistance of a wear layer, and permits immediate intervention into the process.

What is claimed is:

1. A method for determining the abrasion resistance of at least one wear layer arranged on at least one core board comprising the following steps:
   recording at least one NIR spectrum of the at least one wear layer arranged on the at least one core board
   a) before hardening of the at least one wear layer,
   b) after hardening of the at least one wear layer, or
   c) before and after hardening of the at least one wear layer with the at least one core board with use of at least one NIR detector in the wavelength range from 500 nm to 2500 nm;
   by means of multivariate data analysis (MDA), determining the abrasion resistance of the at least one wear layer by comparing the NIR spectrum recorded for determining the abrasion resistance of the at least one wear layer with at least one NIR spectrum recorded for at least one reference sample of the at least one wear layer with known abrasion resistance,
   where the at least one NIR spectrum recorded for the at least one reference sample with known abrasion resistance of the at least one wear layer has been determined in advance a) after hardening or b) before and after hardening with use of the same NIR detector in the wavelength range from 500 nm to 2500 nm.

2. The method as claimed in claim 1, wherein the abrasion resistance of the at least one wear layer is determined before hardening of the wear layer within a production line for the board.

3. The method as claimed in claim 1, wherein the abrasion resistance of the at least one wear layer is determined after hardening of the wear layer outside of a production line for the board.

4. The method as claimed in claim 1, wherein the abrasion resistance of the at least one wear layer is determined before hardening of the wear layer within a production line for the board and after hardening of the wear layer outside of the production line for the board.

5. The method as claimed in claim 1, wherein the abrasion resistance of the at least one wear layer of the at least reference sample has been determined before or after hardening on the basis of at least one individual sample taken from the hardened reference sample.

6. The method as claimed in claim 5, wherein the abrasion resistance of the wear layer of the reference sample is determined on the basis of at least one individual sample taken from the reference sample.

7. The method as claimed in claim 6, wherein the abrasion resistance of the wear layer of the reference sample is determined in accordance with DIN EN 13329:2009 (D).

8. The method as claimed in claim 1, wherein the reference sample with known abrasion resistance of the wear layer comprises a wear layer applied on a core board, where core board and wear layer of the reference sample are of the same type as the test sample made of core board and wear layer.

9. The method as claimed in claim 1, wherein the at least wear one layer is selected from the group comprising a) at least one heat-curable protective layer and/or b) at least one UV-curable and/or electron-beam-curable (EBC) protective layer.

10. The method as claimed in claim 1, wherein the at least one wear layer comprises abrasion-resistant particles.

11. The method as claimed in claim 10, wherein the abrasion-resistant particles are selected from the group comprising aluminum oxides, boron carbides, silicon dioxides and silicon carbides.

12. The method as claimed in claim 1, wherein the at least one wear layer comprises a quantity of from 5 to 100 g/m² of abrasion-resistant particles.

13. The method as claimed in claim 12, wherein the at least one wear layer comprises a quantity of from 20 to 50 g/m² of abrasion-resistant particles.

14. The method as claimed in claim 1, wherein the thickness of the at least one wear layer is from 10 to 150 μm.

15. The method as claimed in claim 14, wherein the thickness of the at least one wear layer is from 30 to 80 μm.

16. The method as claimed in claim 1, wherein the at least one wear layer comprises at least two sublayers.

17. The method as claimed in claim 16, wherein the quantity applied of the sublayers is identical or different.

18. The method as claimed in claim 16, wherein the at least one wear layer comprises at least three sublayers applied in succession.

19. The method as claimed in claim 1, wherein the at least one core board is a wood-composite board.

20. The use of at least one NIR detector for determining the abrasion resistance of the wear layer applied on a core board by a method as claimed in claim 1, within and outside of a production line for producing boards.

\* \* \* \* \*